United States Patent
Rao et al.

(10) Patent No.: US 10,324,058 B2
(45) Date of Patent: Jun. 18, 2019

(54) IN-SITU CHEMISTRY STACK FOR CONTINUOUS GLUCOSE SENSORS

(71) Applicant: Medtronic MiniMed, Inc., Northridge, CA (US)

(72) Inventors: Ashwin K. Rao, West Hills, CA (US); Daniel E. Pesantez, Canoga Park, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 448 days.

(21) Appl. No.: 15/141,446

(22) Filed: Apr. 28, 2016

(65) Prior Publication Data

US 2017/0315077 A1 Nov. 2, 2017

(51) Int. Cl.
*G01N 27/327* (2006.01)
*C12Q 1/00* (2006.01)
(Continued)

(52) U.S. Cl.
CPC ..... *G01N 27/3272* (2013.01); *A61B 5/14532* (2013.01); *A61B 5/14865* (2013.01);
(Continued)

(58) Field of Classification Search
CPC ............ G01N 27/3272; G01N 27/307; A61B 5/14532; A61B 5/14865; A61B 2562/125; C12Q 1/003; C12Q 1/006; C12Q 1/002
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

OTHER PUBLICATIONS

Guiseppi-Elie A., et al., "Design of a Subcutaneous Implantable Biochip for Monitoring of Glucose and Lactate", IEEE Sensors Journal IEEE Service Center, New York, NY, US, vol. 5, No. 3, Jun. 1, 2005, pp. 345-355, XP001231820.
(Continued)

*Primary Examiner* — J. Christopher Ball
(74) *Attorney, Agent, or Firm* — Gates & Cooper LLP

(57) ABSTRACT

Embodiments of the invention provide an in-situ polymerization technique for creating a glucose sensor chemistry stack. An analyte sensor comprises a crosslinked polymer matrix in contact with an electrode. The crosslinked polymer matrix is formed by exposing ultraviolet (UV) light to a polymer matrix mixture comprising a plurality of hydroxyethyl methacrylate (HEMA) monomers, one or more di-acrylate crosslinkers, one or more UV photoinitiators, and an oxidoreductase. The oxidoreductase is covalently linked to the crosslinked polymer matrix. In typical embodiments, the oxidoreductase is a glucose oxidase-acrylate bioconjugate. In one or more embodiments, the analyte sensor apparatus further comprises a glucose limiting membrane positioned over the crosslinked polymer matrix. The glucose limiting membrane is formed by exposing ultraviolet (UV) light to a glucose limiting membrane mixture comprising a plurality of hydroxyethyl methacrylate (HEMA) monomers, one or more di-acrylate crosslinkers, one or more UV photoinitiators, ethylene glycol, and water.

18 Claims, 6 Drawing Sheets

(51) Int. Cl.
  *G01N 27/30* (2006.01)
  *A61B 5/145* (2006.01)
  *A61B 5/1486* (2006.01)

(52) U.S. Cl.
  CPC .............. *C12Q 1/002* (2013.01); *C12Q 1/003* (2013.01); *C12Q 1/006* (2013.01); *G01N 27/307* (2013.01); *A61B 2562/125* (2013.01)

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2012/0088997 A1 | 4/2012 | Guiseppi-Elie | |
| 2014/0286875 A1 | 9/2014 | Gamsey et al. | |
| 2015/0122647 A1* | 5/2015 | Shah .................. G01N 27/3271 204/403.14 |
| 2015/0148647 A1 | 5/2015 | Liu et al. | |

OTHER PUBLICATIONS

Gurel, Ihsan, "Immobilization of Glucose Oxidase and Urease in Hydrogel Matrices", I Jan. 1997, XP055390431, retrieved from the Internet: URL:http://journals.tubitak.gov.tr/chem/issues/kim-97-21-4/kim-21-4-21-97068.pdf [retrieved on Jul. 12, 2017], pp. 387-393.
PCT International Search Report and Written Opinion dated Jul. 28, 2017, International Application No. PCT/US2017/029701.

* cited by examiner

IN-SITU CHEMISTRY STACK FOR CONTINUOUS GLUCOSE SENSORS

CROSS REFERENCE TO RELATED APPLICATIONS

This application is related to U.S. patent application Ser. No. 11/633,254, U.S. patent application Ser. No. 12/184, 046, U.S. patent application Ser. No. 12/345,354, and U.S. patent application Ser. No. 12/572,087, the contents of each of which are herein incorporated by reference.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

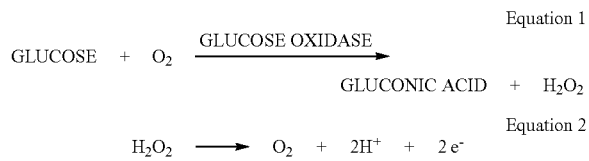

The glucose oxidase is used to catalyze the reaction between glucose and oxygen to yield gluconic acid and hydrogen peroxide (Equation 1). The $H_2O_2$ reacts electrochemically as shown in Equation 2, and the current can be measured by a potentiostat. These reactions, which occur in a variety of oxidoreductases known in the art, are used in a number of sensor designs (see, e.g. Yang et al., Electroanalysis 1997, 9, No. 16: 1252-1256; Clark et al., Ann. N.Y. Acad. Sci. 1962, 102, 29; Updike et al., Nature 1967, 214, 986; and Wilkins et al., Med. Engin. Physics, 1996, 18, 273.3-51). Typically, amperometric sensors comprise a plurality of layered elements including, for example, a base layer having an electrode, an enzyme layer (or analyte sensing layer), and an analyte diffusion control (e.g. glucose limiting membrane/layer).

In addition to the enzyme layer, sensor signal also heavily depends on the diffusion properties of a diffusion control membrane (e.g. glucose limiting membrane (GLM) or glucose limiting layer (GLL)) on the sensor. However, pre-prepared GLM does not allow for the tweaking of GLM diffusion properties on the production floor. It requires re-development of the GLM synthesis protocol. Similarly, many "acrylate-type GLM" currently synthesized in the art do not have glucose diffusion properties that are desirable or tweakable. In addition, the GLM used in sensors that are currently manufactured is hydrophobic in nature, making it difficult to adhere to a hydrophilic GOx or HSA layer. Thus, an adhesion promoter layer (such as (3-Aminopropyl)triethoxysilane (APTES)) is often required to minimize delamination of the GLM layer from the sensor. However, the increased thickness from an adhesion promoter layer can add undesirable bulk to implantable sensors and can also compromise sensor operability by inhibiting an analyte's ability to generate a signal. In addition, the hydrophobicity of typical GLM in the art contributes to undesirable phenomena in situations where in vivo analytes are being measured in an aqueous environment (e.g. the interstitial space). Such phenomena include, for example, slow sensor hydration profiles (i.e. slow sensor initialization/wet-up) and sensor signal drift. Thus, there are a number of issues with GLM described in the art that provide challenges for using them with a number of sensors described in the art (e.g. amperometric glucose sensors comprising platinum back electrode surfaces upon which a plurality of functional coatings are disposed).

SUMMARY OF THE INVENTION

The formulations and processes provided herein address such issues and provide various other advantages over the art. Embodiments of the enzyme layer and diffusion control membrane disclosed herein comprise polymeric materials constructed to exhibit a constellation of material properties that can be used in a variety of contexts and for example, overcome a number of technical problems observed in sensors, such as electrochemical glucose sensors that are implanted in vivo and which utilize the chemical reaction between glucose and glucose oxidase to generate a measurable signal.

In one aspect of the invention, an analyte sensor apparatus is provided. The analyte sensor apparatus comprises a crosslinked polymer matrix in contact with an electrode. The crosslinked polymer matrix is formed in situ by exposing a polymer matrix mixture to ultraviolet (UV) light. This polymer matrix mixture typically comprises a plurality of hydroxyethyl methacrylate (HEMA) monomers, one or more di-acrylate crosslinkers, one or more UV photoinitiators, and an oxidoreductase, and the polymerization is carried out so that the oxidoreductase is covalently linked to the crosslinked polymer matrix. In one or more embodiments, the analyte sensor apparatus further comprises a glucose limiting membrane positioned over the crosslinked polymer matrix. The glucose limiting membrane is formed by exposing ultraviolet (UV) light to a glucose limiting membrane mixture comprising a plurality of hydroxyethyl methacrylate (HEMA) monomers, one or more di-acrylate crosslinkers, one or more UV photoinitiators, ethylene glycol, and water.

In one or more embodiments, the oxidoreductase is a glucose oxidase-acrylate bioconjugate. Typically, the glucose oxidase-acrylate bioconjugate loading in the crosslinked polymer matrix is 10-80 mol %. The glucose oxidase-acrylate bioconjugate is formed by reacting glucose oxidase with acryloyl-PEG-(N-hydroxy succinimide) in a respective mole ratio ranging from 1:1 to 1:10. In one instance, the glucose oxidase is reacted with acryloyl-PEG-(N-hydroxy succinimide) in a respective mole ratio of 1:4. In some embodiments, the di-acrylate crosslinker is triethylene glycol diacrylate (TEGDA) or polyethylene glycol diacrylate (PEGDA). The UV photoinitiator may be 2,2,-dimethoxy-2-phenylacetophenone (DMPA) or a phosphine blend. In further embodiments, the glucose limiting membrane further comprises polyethylene glycol (PEG)-methacrylate, methyl methacrylate, poly(2-hydroxyethyl methacrylate) (poly-HEMA), or methacryloyl phosphorylcholine (MPC).

In another aspect of the invention, a method of producing an analyte sensor apparatus is provided. The method comprises providing a monomer mixture comprising a plurality of hydroxyethyl methacrylate (HEMA) monomers, one or more di-acrylate crosslinkers, one or more UV photoinitiators, and an oxidoreductase. The monomer mixture is then deposited over a sensor substrate and then polymerized in situ with ultraviolet (UV) light to form a crosslinked polymer matrix, thereby entrapping the oxidoreductase within the crosslinked polymer matrix. The mixture to be polymerized is typically deposited using a spin, slot or spray coating method. In certain embodiments, curing the monomer mixture with ultraviolet (UV) light includes masking an area of the deposited monomer mixture to prevent the monomer mixture from polymerizing and forming a crosslinked polymer matrix in that area.

In one or more embodiments, the method further comprises providing a glucose limiting membrane mixture comprising a plurality of hydroxyethyl methacrylate (HEMA) monomers, one or more di-acrylate crosslinkers, one or more UV photoinitiators, ethylene glycol, and water. The glucose limiting membrane mixture is then deposited over the crosslinked polymer matrix and cured with ultraviolet (UV) light to form a glucose limiting membrane.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
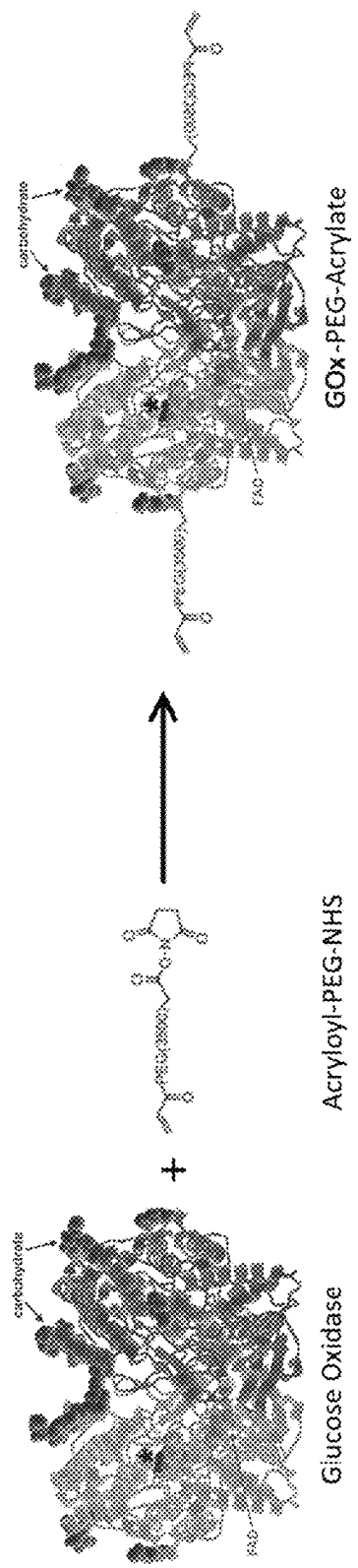
FIG. 1 provides a schematic of the reaction for the preparation of GOx-Acrylate bioconjugate using acryloyl-PEG-NHS compounds, in accordance with one or more embodiments of the invention.

Unless otherwise defined, all terms of art, notations, and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. In addition, certain text from related art is reproduced herein to more clearly delineate the various embodiments of the invention. A number of terms are defined below.

All publications mentioned herein are expressly incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. In one or more embodiments, the oxidoreductase is a glucose oxidase-acrylate bioconjugate. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The terms "electrochemically reactive surface" and "electroactive surface" as used herein are broad terms and are used in their ordinary sense, including, without limitation, the surface of an electrode where an electrochemical reaction takes place. In one example, a working electrode (e.g. one comprised of platinum black) measures the hydrogen peroxide produced by the enzyme-catalyzed reaction of the analyte being detected by creating an electric current. For example, detection of glucose analyte utilizing glucose oxidase produces $H_2O_2$ as a by-product. The $H_2O_2$ reacts with the surface of the working electrode producing two protons ($2H^+$), two electrons ($2e^-$), and one molecule of oxygen ($O_2$) which produces the electronic current being detected. In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. analyte sensing layer, glucose limiting membrane) can be adapted for use with any one of the wide variety of sensors known in the art. The analyte sensor elements, architectures, and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Typical embodiments of the invention include methods for forming a working electrode in an analyte sensor apparatus, methods which include the step of forming a monomer mixture on an electroactive surface of the electrode (optionally using a spin, slot or spray coating method). In such embodiments, the monomer mixture comprises a plurality of hydroxyethyl methacrylate (HEMA) monomers; one or more di-acrylate crosslinkers; one or more UV photoinitiators; and an oxidoreductase (e.g. a glucose oxidase-acrylate bioconjugate designed to make up 10-80 mol % of the crosslinked polymer matrix). This monomer mixture is then polymerized/cured with ultraviolet (UV) light so as to form a crosslinked polymer matrix on the electrode, a material where the oxidoreductase is covalently linked to the crosslinked polymer matrix. Typically, these methods also comprise forming a glucose limiting membrane mixture over the crosslinked polymer matrix (optionally using a spin, slot or spray coating method), the membrane mixture comprising: a plurality of hydroxyethyl methacrylate (HEMA) monomers; one or more di-acrylate crosslinkers; one or more UV photoinitiators; ethylene glycol; and water. This glucose limiting membrane mixture is then polymerized with ultraviolet (UV) light to form a glucose limiting membrane. In certain embodiments, polymerization reactions with ultraviolet (UV) light include the step of masking an area covered by a mixture to be polymerized so as to prevent polymerization at that area.

In some methodological embodiments of the invention, amounts of reagents such as the di-acrylate crosslinker and HEMA monomers are selected and mixed in a specific ratio that is designed to control the cross-link density of the glucose limiting membrane, thereby controlling the glucose permeability of the glucose limiting membrane (e.g. so that the polymeric composition has a glucose permeability of at least $1\times10^{-8}$ cm$^2$/s at 37° C. in phosphate buffered saline). Optionally, the sensor is a glucose sensor of the type typically used by diabetics and the working electrode: comprises a plurality of layers that does not include an adhesion promoting layer and/or comprises a plurality of layers that does not include a separate layer consisting essentially of an albumin and/or comprises a crosslinked polymer matrix formed by a process that does not utilize glutaraldehyde.

Embodiments of the invention also include an analyte sensor apparatus comprising a crosslinked polymer matrix disposed on a working electrode, wherein the crosslinked polymer matrix is formed in-situ on an electroactive surface of the working electrode by exposing a polymerization reaction mixture to ultraviolet (UV) light, wherein the polymerization reaction mixture comprises: a plurality of hydroxyethyl methacrylate (HEMA) monomers; one or more di-acrylate crosslinkers; one or more UV photoinitiators; and an oxidoreductase (e.g. a glucose oxidase-acrylate bioconjugate formed by reacting glucose oxidase with acryloyl-PEG-(N-hydroxy succinimide) in a respective mole ratio ranging from 1:1 to 1:10). In such embodiments, the oxidoreductase is covalently linked to the crosslinked polymer matrix. Typically, this apparatus further includes a glucose limiting membrane disposed over the crosslinked polymer matrix, wherein the glucose limiting membrane is formed in-situ over the crosslinked polymer matrix by exposing a membrane reaction mixture to ultraviolet (UV) light. In such embodiments, the membrane reaction mixture comprises: a plurality of hydroxyethyl methacrylate (HEMA) monomers; one or more di-acrylate crosslinkers; one or more UV photoinitiators; ethylene glycol; and water.

Specific aspects of embodiments of the invention are discussed in detail in the following sections.

I. Typical Elements, Configurations, and Analyte Sensor Embodiments of the Invention In one aspect of the invention, an in-situ polymerization technique is provided for creating a glucose sensor chemistry stack. Generally, the technique involves adding monomers onto a substrate, plate or layer and then polymerizing using a UV method (as opposed to using a prepared polymer and then coating the polymer on a sensor). Thus, instead of a chemistry stack physically adsorbed to an electrode, the chemistry stack is covalently bonded. In one or more embodiments, a UV curable Glucose Oxidase (GOx) process is provided based on the "entrapment" of an oxidoreductase (e.g. GOx, GOx bioconjugate) within a polymer matrix. This UV curable GOx process has several advantages, including the ability to selectively deposit GOx on a sensor working electrode and the elimination of the need for toxic glutaraldehyde and its associated chemical vapor deposition (CVD) process. Certain advantages are lost, however, with UV entrapped GOx when compared to GOx that is covalently crosslinked using a glutaraldehyde crosslinking process. For example, a covalently crosslinked GOx has the benefit of a stable chemical structure when formed as a GOx layer.

Figure 2:
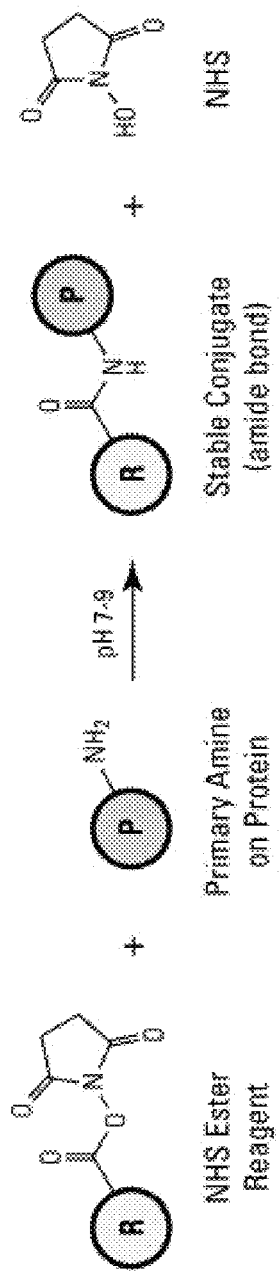
FIG. 2 provides a general schematic of the reaction between primary amines and N-hydroxy-succinimide (NHS) functionalized groups so as to form an amide bonded stable conjugate, in accordance with one or more embodiments of the invention. Such reactions are well known in the art, see, e.g. Easy Molecular Bonding, Reactivity Chemistries, Applications and Structure References, Thermo Scientific, Crosslinking Technical Handbook.

Thus in one or more embodiments of the invention, a GOx bioconjugate is described that provides greater stability when UV entrapped in a polymer matrix. Benefits include long-term stability of the GOx enzyme during in vivo sensor operation and the reduction of sensitivity loss during long-term (e.g. over 6 days) sensor operation. In one preferred embodiment, the GOx bioconjugate is a GOx-Acrylate bioconjugate. FIG. 1 is an illustration of a method for preparing a GOx-Acrylate bioconjugate. GOx reacts with acryloyl-PEG-(N-hydroxy succinimide) at a mole ratio ranging from 1:1 to 1:10. In one instance, the mole ratio is 1:4. The N-hydroxy succinimide (NHS) moiety of the Acryl-PEG-NHS reacts with the primary amines, thereby forming GOx that is functionalized with acrylate groups. The general schematic of the reaction between primary amines and NHS functionalized groups is shown in FIG. 2.

Once the GOx-Acrylate bioconjugate molecule is synthesized, GOx-Acrylate is mixed with hydroxyethyl methacrylate (HEMA) monomer, di-acrylate crosslinker (e.g. triethylene glycol diacrylate (TEGDA) or polyethylene glycol diacrylate (PEGDA)) and UV photoinitiator (e.g. 2,2,-dimethoxy-2-phenylacetophenone (DMPA) or a phosphine blend) to form a monomer mixture. The typical loading of GOx acrylate is about 10-80 mol %. The monomer mixture is then coated onto the sensor substrate via a coating method such as a spin, slot or spray coating method. Selected areas (such as a working electrode) can then be crosslinked using an ultraviolet (UV) light source and masks may be used to block out UV light and prevent crosslinking of specific areas. The sensor is then rinsed with buffer or DI water to remove unreacted monomers and excess photoinitiators.

In another aspect of the invention, a homogenous polymer chemistry stack is provided using a compatible polymer backbone between layers. In one or more embodiments, the sensor is further coated with a diffusion control membrane that has the same polymer backbone structure as the GOx-Acrylate coating. Thus, for example in sensors that are implanted in vivo, embodiments of the enzyme layer and diffusion control membrane function without requiring a thick adhesion promoter layer that substantially increases the bulk of the sensor or compromises sensor operability.

Figure 3:
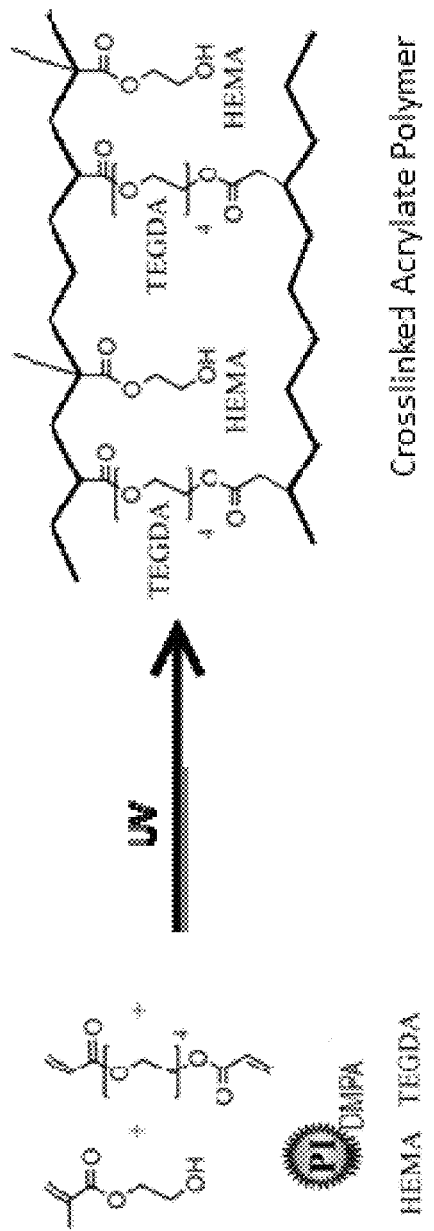
FIG. 3 provides a schematic of the reaction for the preparation of an in-situ polymerized glucose limiting layer using HEMA and TEGDA and an illustrative photoinitiator, along with UV light in order to form a crosslinked acrylate polymer, in accordance with one or more embodiments of the invention.

In one preferred embodiment, an in-situ preparation and coating of a GLM with tailored diffusion properties is provided (see FIG. 3). Hydroxyethyl methacrylate (HEMA) monomer, di-acrylate crosslinker (e.g. triethylene glycol diacrylate (TEGDA) or polyethylene glycol diacrylate (PEGDA)) and UV photoinitiator (e.g. 2,2,-dimethoxy-2-phenylacetophenone (DMPA) or a phosphine blend), ethylene glycol, and DI water are used to prepare a monomer mixture for in-situ GLM. The monomers are then coated on the sensors at a desired thickness over the enzyme layer (e.g. GOx-Acrylate layer). UV light exposure ensures the cross-link is complete to form the in-situ GLM on the sensor. The single base polymer of HEMA inhibits delamination and eliminates the use of an adhesion promoting constituents (AP) and human serum albumin (HAS). The molar ratios of TEGDA vs. HEMA controls the cross-link density of the in-situ GLM, thereby allowing glucose diffusion properties to be tweaked as desired. Various additives may also be added to optimize the structural stability and hydrophilicity of the in-situ GLM. Some examples include: PEG-methacrylate to add hydrophilicity; methyl methacrylate to reduce hydrophilicity; polyHEMA to add structural stability; and methacryloyl phosphorylcholine (MPC) to add biomimetic or biocompatible properties.

One illustrative embodiment of the invention is an amperometric analyte sensor apparatus (e.g. one designed for implantation within a mammal) comprising a crosslinked polymer matrix in contact with an electrode. The crosslinked polymer matrix is formed in situ by exposing ultraviolet (UV) light to a polymer matrix mixture comprising a plurality of hydroxyethyl methacrylate (HEMA) monomers, one or more di-acrylate crosslinkers, one or more UV photoinitiators, and an oxidoreductase. In this way, the oxidoreductase is covalently linked to the crosslinked polymer matrix. In one or more embodiments, the analyte sensor apparatus further comprises a glucose limiting membrane positioned over the crosslinked polymer matrix. The glucose limiting membrane is formed by exposing ultraviolet (UV) light to a glucose limiting membrane mixture comprising a plurality of hydroxyethyl methacrylate (HEMA) monomers, one or more di-acrylate crosslinkers, one or more UV photoinitiators, ethylene glycol, and water. In addition to simplifying and reducing the costs of sensor production, embodiments of the invention where both the crosslinked polymer matrix and the glucose limiting membrane that is positioned over the crosslinked polymer matrix are formed in situ as described immediately above exhibit a number of unexpected and desirable characteristics such as better layer adhesion. While not bound by any specific mechanism or theory of action, this enhanced adhesion may be the result of the crosslinked polymer matrix and the glucose limiting membrane layers being formed in a way that creates a more homogeneous stack of sensor material layers (thereby inhibiting delamination etc.).

Typically, the analyte sensing layer or enzyme layer comprises an oxidoreductase (e.g. glucose oxidase) that generates hydrogen peroxide upon exposure to a substrate for the oxidoreductase (e.g. glucose), wherein the amount of hydrogen peroxide generated by the oxidoreductase is proportional to the amount of substrate exposed to the oxidoreductase. In one or more embodiments, the oxidoreductase is a glucose oxidase-acrylate bioconjugate. Typically, the glucose oxidase-acrylate bioconjugate loading in the crosslinked polymer matrix is 10-80 mol %. The glucose oxidase-acrylate bioconjugate is formed by reacting glucose oxidase with acryloyl-PEG-(N-hydroxy succinimide) in a respective mole ratio ranging from 1:1 to 1:10. In one instance, the glucose oxidase is reacted with acryloyl-PEG-(N-hydroxy succinimide) in a respective mole ratio of 1:4. In some embodiments, the di-acrylate crosslinker is triethylene glycol diacrylate (TEGDA) or polyethylene glycol diacrylate (PEGDA). The UV photoinitiator may be 2,2,-dimethoxy-2-phenylacetophenone (DMPA) or a phosphine blend. In further embodiments, the glucose limiting membrane further comprises polyethylene glycol (PEG)-methacrylate, methyl methacrylate, poly(2-hydroxyethyl methacrylate) (polyHEMA), or methacryloyl phosphorylcholine (MPC).

In certain embodiments of the invention, the crosslinked polymers are adhered to a surface of an electrode that comprises an irregular architecture characteristic of an electrodeposition process (e.g. platinum black). In some embodiments, a first side of the analyte sensing layer (e.g. one comprising glucose oxidase) is in direct contact with an electrochemically reactive surface of a working electrode; and a GLM is in direct contact with a second side of the analyte sensing layer.

Optionally, embodiments of the invention further include one or more of: a protein layer disposed on the analyte sensing layer; an analyte modulating layer disposed on the analyte sensing layer or the protein layer, wherein the analyte modulating layer comprises a composition that modulates the diffusion of an analyte such as glucose diffusing through the analyte modulating layer; an adhesion promoting layer disposed on the analyte sensing layer, wherein the adhesion promoting layer promotes the adhesion between the analyte sensing layer and an analyte modulating layer; or a cover layer disposed on the analyte sensor apparatus, wherein the cover layer comprises an aperture positioned on the cover layer so as to facilitate an analyte present in the mammal accessing and diffusing through an analyte modulating layer; and accessing the analyte sensing layer.

Figure 5A:
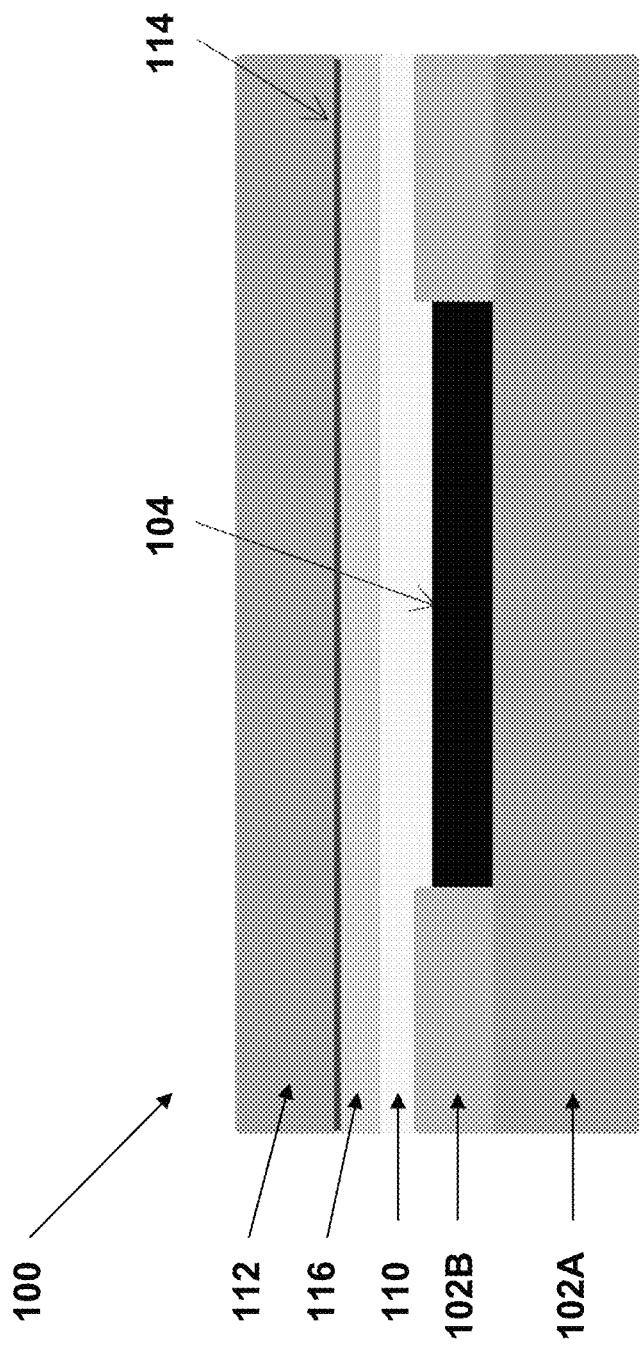
FIG. 5A provides a diagrammatic view of one embodiment of an amperometric analyte sensor to which an interference rejection membrane can be added (e.g. disposed on conductive layer/electrode 104).
Figure 5B:
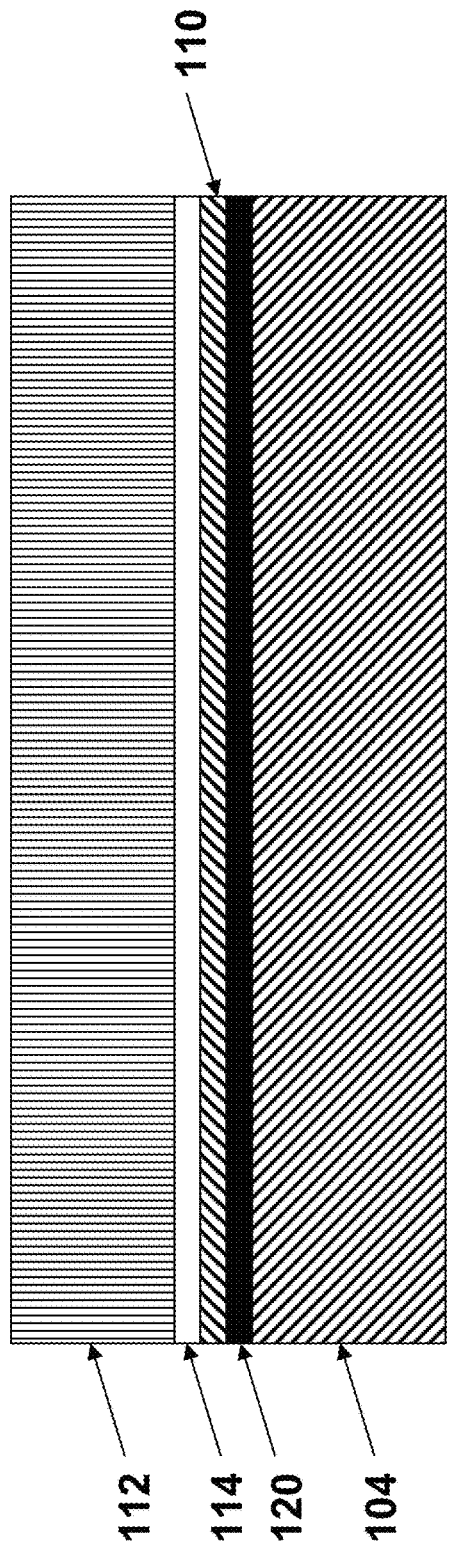
FIG. 5B provides a diagrammatic view of another embodiment of an amperometric analyte sensor having an interference rejection membrane.

In some sensor embodiments, an adhesion promoter layer is still added to facilitate close attachment of various layers such as a diffusion control membrane and an enzyme layer. One such sensor embodiment is shown in FIG. 5A. Certain embodiments of the invention disclosed herein further include an interference rejection membrane (IRM) that is designed to inhibit and/or prevent endogenous or exogenous electroactive substances in vivo (e.g. in interstitial fluid). These endogenous or exogenous electroactive substances, such as acetaminophen, uric acid, and ascorbic acid, are inhibited and/or prevented from accessing the sensor electrode and being oxidized at the electrode surface, which would consequently produce a spurious signal that can confound measurements of the signal generated by the analyte to be measured. One illustrative embodiment of a sensor having an interference rejection membrane is shown in FIG. 5B.

In some embodiments of the invention, the conductive layer comprises a plurality of electrodes including the working electrode, a counter electrode and a reference electrode. Optionally, the conductive layer comprises a plurality of working electrodes, counter electrodes and reference electrodes; and the plurality of working, counter, and reference electrodes are grouped together as a unit and positionally distributed on the conductive layer in a repeating pattern of units. In some embodiments of the invention, the sensor is operatively coupled to: a sensor input capable of receiving a signal from the sensor that is based on a sensed physiological characteristic value in the mammal; and a processor coupled to the sensor input, wherein the processor is capable of characterizing one or more signals received from the sensor. In certain embodiments of the invention, a pulsed voltage is used to obtain a signal from an electrode.

Another aspect of the invention is a method of making an analyte sensing system or sensor apparatus having the constellation of elements and/or made by the methodological steps disclosed herein. In one or more embodiments, the method comprises providing a monomer mixture comprising a plurality of hydroxyethyl methacrylate (HEMA)

monomers, one or more di-acrylate crosslinkers, one or more UV photoinitiators, and an oxidoreductase. The monomer mixture is then deposited over a sensor substrate and then cured with ultraviolet (UV) light to form a crosslinked polymer matrix, thereby embedding the oxidoreductase within the crosslinked polymer matrix. In one or more embodiments, the method further comprises providing a glucose limiting membrane mixture comprising a plurality of hydroxyethyl methacrylate (HEMA) monomers, one or more di-acrylate crosslinkers, one or more UV photoinitiators, ethylene glycol, and water. The glucose limiting membrane mixture is then deposited over the crosslinked polymer matrix and cured with ultraviolet (UV) light to form a glucose limiting membrane.

The polymeric compositions of the invention can be formed using a variety of art-accepted processes. Typically, the monomer mixture is deposited on the sensor substrate using a spin, slot or spray coating method, for example as a single or multilayered coating over a substrate wafer. Membrane coating conditions include the spin coating RPM, the membrane thickness, as well as the time exposed to UV light. In certain embodiments, curing the monomer mixture with ultraviolet (UV) light includes masking an area of the deposited monomer mixture to prevent the monomer mixture from forming a crosslinked polymer matrix over the sensor substrate. Such methods provide an easy sensor manufacturing process by reducing the equipment needed and process steps. A highly controllable UV crosslinking process may be conducted using existing equipment in the art. This eliminates complex/expensive CVD equipment and toxic glutaraldehyde. Biocompatibility of the sensor is also enhanced by use of materials like pHEMA, TEGDA, etc. which are known to be highly biocompatible.

A. Typical Sensor Architectures Found in Embodiments of the Invention

FIG. 5A illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIGS. 5A-B. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 5A includes a base layer 102A to support the sensor 100. The base layer 102A can be made of a material such as a metal and/or a ceramic and/or a polymeric substrate, which may be self-supporting or further supported by another material as is known in the art. Typically, the base layer 102A comprises polyimide. Embodiments of the invention include a conductive layer 104 which is disposed on and/or combined with the base layer 102A. Typically, the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102A and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer such as a polymer coating or an insulator 102B can be disposed on portions of the sensor 100. Acceptable polymer coatings for use as the insulating cover layer or the insulator 102B can include, but are not limited to, non-toxic biocompatible polymers such as silicone compounds, polyimides, biocompatible solder masks, epoxy acrylate copolymers, or the like. Typically, the insulator 102B comprises polyimide. Insulator 102B may be used to electrically insulate the conductive layer 104 from the external environment or other electrodes. In other embodiments of the sensors of the present invention, one or more exposed regions or apertures can be made through the cover layer to open the conductive layer 104 to the external environment and to, for example, allow an analyte such as glucose to permeate the layers of the sensor and be sensed by the sensing elements. Apertures can be formed by a number of techniques, including laser ablation, tape masking, chemical milling or etching or photolithographic development or the like. In certain embodiments of the invention, during manufacture, a secondary photoresist can also be applied to the protective layer to define the regions of the protective layer to be removed to form the aperture(s). The exposed electrodes and/or contact pads can also undergo secondary processing (e.g. through the apertures), such as additional plating processing, to prepare the surfaces and/or strengthen the conductive regions.

In the sensor configuration shown in FIG. 5A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 5B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic™ MiniMed™.

In embodiments of the invention, the analyte sensing layer 110 can be applied over portions of the conductive layer 104 or over the entire region of the conductive layer 104. The analyte sensing layer 110 can also be applied over the insulator 102B. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the monomer mixture to be crosslinked onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and/or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting layer or membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels or any other suitable hydrophilic membranes known to those skilled in the art.

In some embodiments of the invention, an adhesion promoter layer 114 is disposed between the analyte modulating layer 112 and the analyte sensing layer 110 as shown in FIG. 5B in order to further facilitate their contact and/or adhesion. In some embodiments of the invention, an adhesion promoter layer 114 is disposed between the analyte modulating layer 112 and a protein layer 116 as shown in FIG. 5A in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In preferred embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described herein.

Base Constituent

Sensors of the invention typically include a base constituent (see, e.g. element 102 in FIG. 5A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 5A, the base constituent 102 comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 5A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent. Examples of useful materials for generating this protective cover constituent include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids, such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size).

Examples of interference rejection constituents include one or more layers or coatings of compounds such as the hydrophilic crosslinked pHEMA polymers, polylysine polymers, cellulose acetate (including cellulose acetate incorporating agents such as poly(ethylene glycol)), polyethersulfones, polytetra-fluoroethylenes, the perfluoronated ionomer NAFION™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

Additional compositions having an unexpected constellation of material properties that make them ideal for use as interference rejection membranes in certain amperometric glucose sensors as well as methods for making and using them are further disclosed herein.

Analyte Sensing Constituent

The electrochemical sensors of the invention include an analyte sensing constituent disposed on the electrodes of the sensor (see, e.g. element 110 in FIG. 5A). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with, for example, the coated surface of the working electrode being larger than the coated surface of the counter and/or reference electrode.

Figure 4:
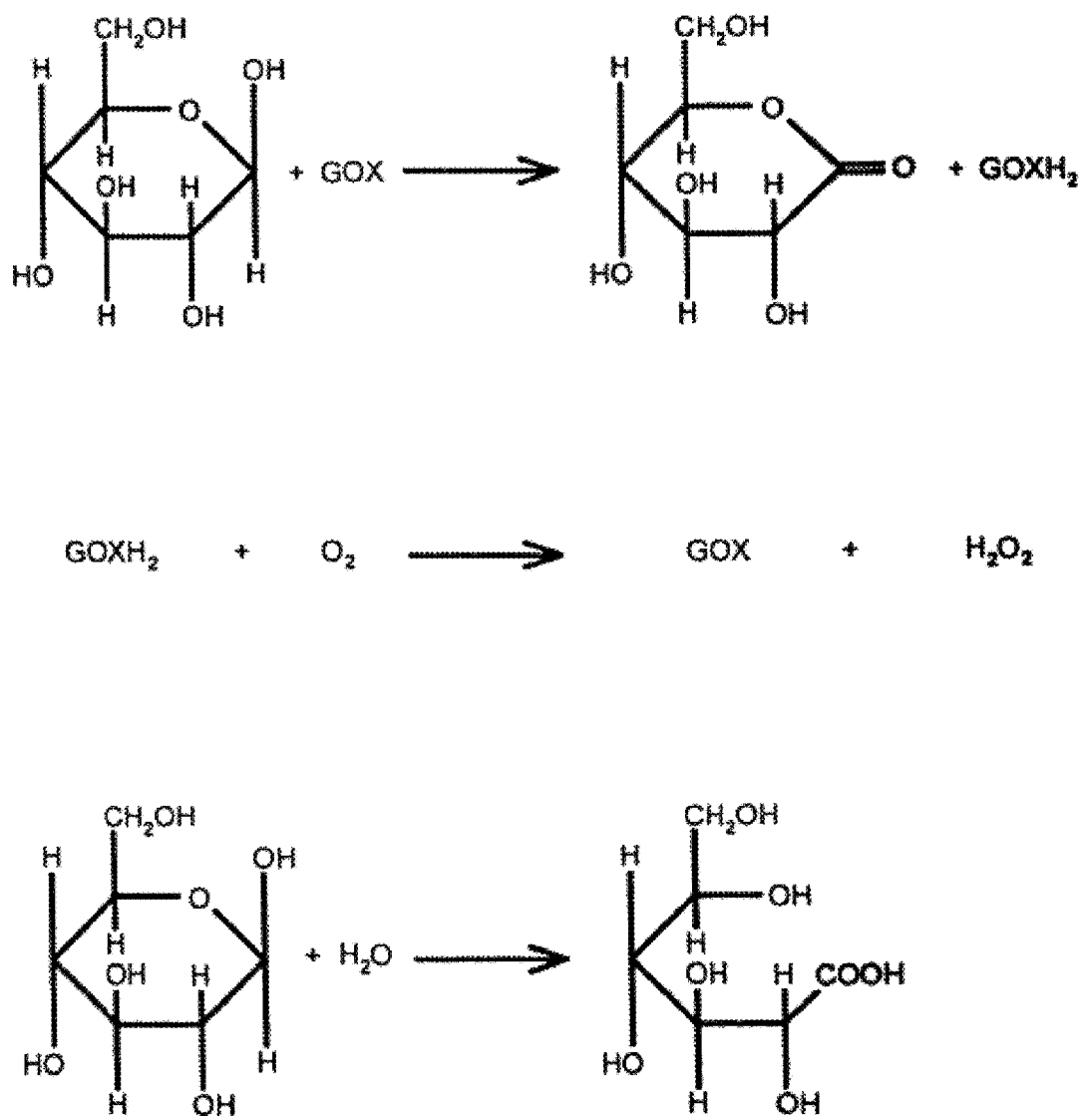
FIG. 4 provides a schematic of the reaction between glucose and glucose oxidase. As shown in a stepwise manner, this reaction involves glucose oxidase (GOx), glucose, and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 30\ 2e^-$).

Typical sensor embodiments of this element of the invention utilize an enzyme (e.g. glucose oxidase) included in a polymer matrix mixture that is applied on the surface of an electrode and subsequently exposed to UV light to form a thin crosslinked polymer matrix with the enzyme covalently linked to this matrix. In a typical embodiment of an analyte sensing layer having GOx, the GOx reacts with glucose present in the sensing environment (e.g. the body of a mammal) and generates hydrogen peroxide according to the reaction shown in FIG. 4, wherein the hydrogen peroxide so generated is anodically detected at the working electrode in the conductive constituent. In preferred embodiments, the GOx is a GOx-Acrylate bioconjugate.

Protein Constituent

The electrochemical sensors of the invention optionally include a protein constituent disposed between the analyte sensing constituent and the analyte modulating constituent (see, e.g. element 116 in FIG. 5A). The term "protein constituent" is used herein according to art accepted terminology and refers to a constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically, the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can optionally include one or more adhesion promoting (AP) constituents (see, e.g. element 114 in FIG. 5A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such as the analyte sensing constituent and/or the protein constituent and/or a siloxane moiety present in a compound disposed in a proximal layer such as the analyte modulating layer.

Anayte Modulating Constituent

The electrochemical sensors of the invention include an analyte modulating constituent disposed on the sensor (see, e.g. element 112 in FIG. 5A). The term "analyte modulating constituent" is used herein according to art accepted terminology and refers to a constituent that typically forms a membrane on the sensor that operates to modulate the diffusion of one or more analytes, such as glucose and/or O$_2$, through the constituent. In certain embodiments of the invention, the analyte modulating constituent is an analyte-limiting membrane or diffusion control membrane (e.g. a glucose limiting membrane (GLM)) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. O$_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771, 868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent. In preferred embodiments, the diffusion control membrane has the same polymer backbone structure as the analyte sensing constituent.

Cover Constituent

The electrochemical sensors of the invention include one or more cover constituents which are typically electrically insulating protective constituents. Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors disclosed herein can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver periodically (e.g. every 5 minutes) to provide providing real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include, for example, the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values include a plurality of measurements of blood glucose.

D. Embodiments of the Invention and Associated Characteristics

Embodiments of the invention disclosed herein focus on implantable analyte sensors and sensor systems that are designed to include hydrophilic compositions (e.g. an interference rejection membrane comprising polymers crosslinked by a hydrophilic crosslinking agent) and/or configurations of elements that facilitate sensor initialization and/or start-up in vivo (e.g. the run-in time that it takes for a sensor to settle into its aqueous environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two-hour start-up period which can be an inconvenience in view of a patient's active daily routine. For these reasons, sensors and sensor systems that are designed to include elements and/or configurations of elements can reduce sensor initialization and/or start-up times (e.g. the hydrophilic interference rejection membranes disclosed herein) are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

The invention disclosed herein has a number of embodiments. One illustrative embodiment of the invention is an analyte sensor apparatus comprising: an elongated (i.e. having notably more length than width) base layer; a conductive layer disposed on the base layer and comprising a reference electrode, a working electrode and a counter electrode; an interference rejection membrane disposed upon the conductive layer, an analyte sensing layer disposed on the interference rejection membrane; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte accessing and diffusing through the analyte modulating layer and accessing the analyte sensing layer. Typical embodiments of the invention are comprised of biocompatible materials and/or have structural features designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more functions of the sensor embodiments disclosed herein.

As disclosed herein, those of skill in the art understand that a conductive layer disposed on the base layer and comprising a working electrode, a counter electrode and a reference electrode includes embodiments wherein the conductive layer is disposed on at least a portion the base layer and does not necessarily completely cover the base layer. Those of skill in the art will understand that this refers to other layers within the sensor, with for example, an analyte sensing layer disposed on the conductive layer encompassing sensor embodiments where the analyte sensing layer disposed on at least a portion of the conductive layer; and an analyte modulating layer disposed on the analyte sensing layer encompassing an analyte modulating layer disposed on at least a portion of the analyte sensing layer etc. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1X reference electrode, a 2.6X working electrode and a 3.6X counter electrode.

In certain embodiments of the invention, an element of the apparatus such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromise sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like).

Typical analyte sensor apparatus embodiments comprise a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid accessing at least one of working electrode as the sensor apparatus twists and bends when implanted in vivo. In some embodiments, the electrodes are grouped in a configuration that allows the sensor to continue to maintain an optimal function if a portion of the sensor having one or more electrodes is dislodged from an in vivo environment and exposed to an ex vivo environment.

Optionally, embodiments of the invention include a plurality of working electrodes and/or counter electrodes and/or reference electrodes (e.g. to provide redundant sensing capabilities). Such embodiments of the invention can be used in embodiments of the invention that include a processor (e.g. one linked to a program adapted for a signal subtraction/cancellation process) are designed factor out background signals in vivo, for example by comparing signal(s) at GOx coated working electrode with signal at working electrode not coated with GOx (e.g. background detection followed by a signal subtraction/cancellation process to arrive at a true signal). Certain of these embodiments of the invention are particularly useful for sensing glucose at the upper and lower ends of the glucose signal curves. Similar embodiments of the invention are used to factor out interference, for example by comparing signal(s) at GOx coated working electrode with signal at working electrode not coated with GOx. Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition). Prussian Blue formulas are known in the art and include Fe4[Fe(CN6]3 xH20, CI no. 77510 and KFe[Fe(Cn)6]xH20 id CI no. 77520.

In typical embodiments of the invention, the sensor is operatively coupled to further elements (e.g. electronic components) such as elements designed to transmit and/or receive a signal, monitors, pumps, processors and the like. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase (and optionally two are coated with GOx) and at least one working electrode is not coated with an analyte sensing layer comprising glucose oxidase. Such embodiments of the invention can be used for example in sensor embodiments designed factor out background signals in vivo, for example by comparing signal(s) at GOx coated working electrode(s) with signal at working electrode(s) not coated with GOx (e.g. background detection followed by a signal subtraction/cancellation process to arrive at a true signal).

In some embodiments of sensors insertion set apparatuses, a first and a second (and/or third etc.) electrochemical sensor comprises one working, counter and reference electrode. Alternatively, the plurality of electrochemical sensors comprise a plurality of working, counter and reference electrodes, for example those having a distributed configuration as disclosed in U.S. patent application Ser. No. 11/633,254, the contents of which are incorporated by reference. In certain embodiments of the invention, at least two in the plurality of sensors are designed to measure a signal generated by the same physiological characteristic, for example blood glucose concentration. Embodiments of the invention can include, for example, a plurality of electrochemical sensors having a working electrode coated with an oxidoreductase such as glucose oxidase and are used in methods designed to sample and compare glucose concentrations observed at the plurality of in vivo insertion sites. Alternatively, at least two in the plurality of sensors in the sensor apparatus are designed to measure signals generated by the different characteristics, for example a first characteristic comprising a background or interfering signal that is unrelated to blood glucose (e.g. "interferent noise") and a second characteristic comprising blood glucose concentrations. In an illustrative embodiment of this invention, a first sensor is designed to measure glucose oxidase and comprises one or more working electrodes coated with glucose oxidase while a second comparative sensor is designed to measure a background or interfering signal that is unrelated to blood glucose has no working electrode (or electrodes) coated with glucose oxidase.

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied (e.g. switched) voltage is used to obtain a signal from a working electrode. Typically, at least one voltage is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode.

Sensors of the invention can also be incorporated in a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The sensors of the invention therefore overcome the difficulties observed with such oxygen sensors in non-vascular regions.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include designing an appropriate sensor configuration comprising a working electrode which is an anode, a counter electrode which is a cathode and a reference electrode, and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger or smaller than the counter electrode (cathode) and/or the coated surface of the counter electrode (e.g. a sensor designed to have a 1X area for a reference electrode, a 2.6X area for a working electrode and a 3.6X area for a counter electrode). In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 4), hydrogen peroxide that is produced by an enzyme such as glucose oxidase or lactate oxidase upon reaction with glucose or lactate respectively.

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.,: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.,: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming a interference rejection membrane on the conductive layer, forming an analyte sensing layer on the interference rejection membrane, wherein the analyte sensing layer includes a composition that can alter the electrical current at the electrode in the conductive layer in the presence of an analyte; forming an analyte modulating layer disposed on the analyte sensing layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

In one embodiment, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose oxidase-acrylate bioconjugate, glucose dehydrogenase, lactate oxidase, hexokinase and lactate dehydrogenase.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

Embodiments of the invention can include forming an interference rejection layer on the conductive layer. Briefly for example, one can form an interference rejection membrane using a pHEMA composition comprising 95% C2H5OH and 5% H2O as the solvent system for pHEMA for a spray application process. Alternatively, 95% 2-Butanol and 5% H2O can be another choice for a spray application process, on that exhibits slower evaporation. In such application processes, the concentration of pHEMA typically ranges from 0.25% to 4% by weight, with crosslinker content typically ranging from 0.2% to 0.4% (which can, for example, be determined via the dispensing method). Such processes can include a heating/curing step. In typical embodiments, the heating temperature for curing the membrane can range from 150° C. to 220° C. for a time around 2-15 minutes (e.g. 6 minutes). A wide variety of permutations of such methods will be apparent to artisans. For example, in some embodiments, on can apply the interference rejection membrane by spraying a 0.3-1% Mw 300 kd pHEMA solution (e.g. 0.5%) and 0.25% to 0.4% (0.275%) silane crosslinker. Alternatively, artisans can use a spin coating process with a 1-3% 300 kd pHEMA solution and a silane crosslinker concentration of 0.3% to 0.4%, at a spin speed of 1000 rpm for 30 seconds to generate a single layer. Alternatively, artisans can use a slot coating process with a 4% 200 kd pHEMA solution and a silane crosslinker concentration of 0.35% to 0.5%, and 2 pass coating process to generate multiple layers.

In an illustrative sensor embodiment for use as a glucose sensor, an enzyme (typically glucose oxidase) is coated with the enzyme so as to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor. Methods for producing the enzyme coatings include spin coating processes, dip and dry processes, low shear spraying processes, ink-jet printing processes, silk screen processes and the like. Typically, such coatings are UV crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes.

In some embodiments of the invention, the sensor is made by methods which apply an analyte modulating layer that comprises a hydrophilic membrane coating which can regulate the amount of analyte that can access the enzyme of the sensor layer. For example, the cover layer that is added to the glucose sensors of the invention can comprise a glucose limiting membrane, which regulates the amount of glucose that access glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, NAFION, polyester sulfonic acids (e.g. Kodak AQ), hydrogels or any other membrane known to those skilled in the art that is suitable for such purposes. In certain embodiments of the invention, the analyte modulating layer comprises hydroxyethyl methacrylate (HEMA) monomer, di-acrylate crosslinker (e.g. triethylene glycol diacrylate (TEGDA) or polyethylene glycol diacrylate (PEGDA)) and UV photoinitiator (e.g. 2,2,-dimethoxy-2-phenylacetophenone (DMPA) or a phosphine blend). In other embodiments, a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate hydrogen peroxide molecules and accessing the electrode sensing elements.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

One illustrative embodiment of the invention is a method of making a sensor electrode by providing an electroactive surface which can function as an electrode (e.g. platinum), forming an interference rejection membrane on the electroactive surface, spin coating an enzyme layer on the IRM and then forming an analyte contacting layer (e.g. an analyte modulating layer such as a glucose limiting membrane) on the electrode, wherein the analyte contacting layer regulates the amount of analyte that can contact the enzyme layer. In preferred methods, the enzyme layer is UV crosslinked on the sensor layer. In a typical embodiment of the invention, a sensor is formed to include at least one working electrode and at least one counter electrode. In certain embodiments, the IRM is formed on at least a portion of the working electrode and at least a portion of the counter electrode. Typically, the enzyme layer comprises one or more enzymes such as glucose oxidase, glucose-oxidase-acrylate bioconjugate, glucose dehydrogenase, lactate oxidase, hexokinase or lactate dehydrogenase and/or like enzymes. In one method, the enzyme layer comprises glucose oxidase that is stabilized by coating it on the sensor layer in combination with a carrier protein in a fixed ratio. Typically, the carrier protein is albumin. Typically, such methods include the step of forming an adhesion promoter layer disposed between the glucose oxidase layer and the analyte contacting layer. Optionally, a layer such as the IRM and/or the adhesion promoter layer is subjected to a curing process prior to the formation of the analyte contacting layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

Related embodiments of the invention include a method of sensing an analyte within the body of a mammal, the method comprising implanting an analyte sensor embodiment disclosed herein in to the mammal and then sensing one or more electrical fluctuations such as alteration in current at the working electrode and correlating the alteration in current with the presence of the analyte, so that the analyte is sensed. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example, in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

The invention claimed is:

1. An analyte sensor apparatus comprising:
a crosslinked polymer matrix disposed on a working electrode, wherein the crosslinked polymer matrix is formed in-situ on an electroactive surface of the working electrode by exposing a polymerization reaction mixture to ultraviolet (UV) light, wherein:
(a) the polymerization reaction mixture comprises:
a plurality of hydroxyethyl methacrylate (HEMA) monomers;
one or more di-acrylate crosslinkers;
one or more UV photoinitiators; and
glucose oxidase; and
(b) the polymerization reaction mixture is exposed to the (UV) light so that the glucose oxidase is covalently linked to the crosslinked polymer matrix,
the analyte sensor apparatus further comprising:
a glucose limiting membrane disposed over the crosslinked polymer matrix, wherein the glucose limiting membrane is formed in-situ over the crosslinked polymer matrix by exposing a membrane reaction mixture to ultraviolet (UV) light, wherein:
the membrane reaction mixture comprises:
a plurality of hydroxyethyl methacrylate (HEMA) monomers;
one or more di-acrylate crosslinkers;
one or more UV photoinitiators;
ethylene glycol; and
water.

2. The apparatus of claim 1, wherein the glucose oxidase comprises a glucose oxidase-acrylate bioconjugate.

3. The apparatus of claim 2, wherein the glucose oxidase-acrylate bioconjugate comprises 10-80 mol % of the crosslinked polymer matrix.

4. The apparatus of claim 2, wherein the glucose oxidase-acrylate bioconjugate is formed by reacting glucose oxidase with acryloyl-PEG-(N-hydroxy succinimide) in a respective mole ratio ranging from 1:1 to 1:10.

5. The apparatus of claim 4, wherein the glucose oxidase is reacted with acryloyl-PEG-(N-hydroxy succinimide) in a respective mole ratio of 1:4.

6. The apparatus of claim 1, wherein the di-acrylate crosslinker comprises an ethylene glycol.

7. The apparatus of claim 1, wherein the UV photoinitiator is 2,2,-dimethoxy-2-phenylacetophenone (DMPA) or a phosphine blend.

8. The apparatus of claim 1, wherein the glucose limiting membrane comprises a polyethylene glycol (PEG)-methacrylate, a methyl methacrylate, a poly(2-hydroxyethyl methacrylate) (polyHEMA), and/or a methacryloyl phosphorylcholine (MPC).

9. A method of forming a working electrode in an analyte sensor apparatus, the method comprising:
(a) forming a monomer mixture on an electroactive surface of the electrode, the monomer mixture comprising:
a plurality of hydroxyethyl methacrylate (HEMA) monomers;
one or more di-acrylate crosslinkers;
one or more UV photoinitiators; and
glucose oxidase;
(b) polymerizing the monomer mixture with ultraviolet (UV) light so as to form a crosslinked polymer matrix on the electrode, wherein the glucose oxidase is covalently linked to the crosslinked polymer matrix;
(c) forming a glucose limiting membrane mixture over the crosslinked polymer matrix, the membrane mixture comprising:
a plurality of hydroxyethyl methacrylate (HEMA) monomers;
one or more di-acrylate crosslinkers;
one or more UV photoinitiators:
ethylene glycol; and
water; and
(d) polymerizing the glucose limiting membrane mixture with ultraviolet (UV) light to form a glucose limiting membrane.

10. The method of claim 9, wherein the membrane mixture is deposited over the crosslinked polymer matrix using a spin, slot or spray coating method.

11. The method of claim 9, wherein polymerizing the monomer mixture with ultraviolet (UV) light comprises masking an area of the deposited monomer mixture so as to prevent the monomer mixture from forming a crosslinked polymer matrix over a sensor substrate area.

12. The method of claim 9, wherein the glucose oxidase is a glucose oxidase-acrylate bioconjugate.

13. The method of claim 12, wherein the glucose oxidase-acrylate bioconjugate comprises 10-80 mol % of the crosslinked polymer matrix.

14. The method of claim 12, wherein the glucose oxidase-acrylate bioconjugate is formed by reacting glucose oxidase with acryloyl-PEG-(N-hydroxy succinimide) in a respective mole ratio ranging from 1:1 to 1:10.

15. The method of claim 14, wherein the glucose oxidase is reacted with acryloyl-PEG-(N-hydroxy succinimide) in a respective mole ratio of 1:4.

16. The method of claim 9, wherein amounts of the di-acrylate crosslinker and amounts of HEMA monomers are selected so as to control the cross-link density of the crosslinked glucose limiting membrane, thereby controlling the glucose permeability of the glucose limiting membrane.

17. The method of claim 9, wherein the working electrode:
(a) comprises a plurality of layers that does not include an adhesion promoting layer;
(b) comprises a plurality of layers that does not include a separate layer consisting essentially of an albumin; and/or
(c) comprises a crosslinked polymer matrix formed by a process that does not use glutaraldehyde.

18. The method of claim 9, wherein the glucose limiting membrane further comprises polyethylene glycol (PEG)-methacrylate, methyl methacrylate, poly(2-hydroxyethyl methacrylate) (polyHEMA), or methacryloyl phosphorylcholine (MPC).

* * * * *